United States Patent [19]

Elliott

[11] Patent Number: 4,858,611
[45] Date of Patent: Aug. 22, 1989

[54] SENSING SYSTEM AND METHOD FOR SENSING MINUTE VENTILATION

[75] Inventor: Clyde D. Elliott, Mountain Brook, Ala.

[73] Assignee: Dimed, Inc., Birmingham, Ala.

[21] Appl. No.: 57,492

[22] Filed: Jun. 3, 1987

[51] Int. Cl.$^4$ .......................... A61N 1/00; H05G 00/00
[52] U.S. Cl. ................................ 128/419 P; 128/675
[58] Field of Search .............. 128/419 D, 419 P, 675, 128/419 PG, 716

[56] References Cited

U.S. PATENT DOCUMENTS

| | | | |
|---|---|---|---|
| 2,976,865 | 3/1961 | Shipley | 128/675 |
| 3,273,447 | 9/1966 | Frank | 128/675 |
| 3,593,718 | 7/1971 | Krasner et al. | 128/419 P |
| 3,971,364 | 7/1976 | Fletcher et al. | 128/419 P |
| 4,003,370 | 1/1977 | Knoll et al. | 128/2.05 |
| 4,088,138 | 5/1978 | Diack et al. | 128/419 D |
| 4,102,332 | 7/1978 | Gessman | 128/419 D |
| 4,145,921 | 3/1979 | Blackwelder | 73/170 |
| 4,428,378 | 1/1984 | Anderson et al. | 128/419 PG |
| 4,535,774 | 8/1985 | Olson | 128/419 PG |
| 4,566,456 | 1/1986 | Plicchi et al. | 128/419 PG |
| 4,567,892 | 2/1986 | Koning et al. | 128/419 PG |
| 4,576,183 | 3/1986 | Plicchi et al. | 128/419 PG |
| 4,596,257 | 6/1986 | Plicchi et al. | 128/419 PG |
| 4,600,017 | 7/1986 | Schroeppel | 128/675 |
| 4,719,920 | 1/1988 | Alt et al. | 128/419 G |
| 4,730,618 | 3/1988 | Lekholm et al. | 128/697 |

OTHER PUBLICATIONS

The Exercise-Responsive Cardiac Pacemaker by Geddes et al, IEEE Trans. Biomed Eng, Dec. 84, pp. 763-770.

Funke, H. D., Ein Herzschrittmacher mit belastungsabhangiger Frequenzregulation, 6/1975, Biomedizinche Technik, pp. 225-228 and informal English translation.

*Primary Examiner*—Francis Jaworski
*Assistant Examiner*—George Manuel
*Attorney, Agent, or Firm*—John P. White; Thomas G. Carulli; Peter A. Luccarelli

[57] ABSTRACT

A sensing system for detecting the frequency and amplitude of motion of a patient's diaphragm, having a transducer for detecting movement, transvenously implantable in a patient's cardiovascular system; a lead coupled to the transducer, transvenously implanatable in a patient's cardiovascular system; and a sensing instrument coupled to the lead for correlating transducer movement with the frequency and amplitude of diaphragm motion. A method for sensing the frequency and amplitude of motion of a patient's diaphragm including transvenously implanting in a patient's cardiovascular system a transducer capable of measuring movement frequency and amplitude; detecting the frequency and amplitude of movement of the transducer; and correlating transducer movement with the frequency and amplitude of the patient's diaphragm movement.

22 Claims, 3 Drawing Sheets

SENSING SYSTEM AND METHOD FOR SENSING MINUTE VENTILATION

BACKGROUND OF THE INVENTION

The invention relates generally to the field of cardiac pacers, and more particularly to sensing systems and methods for sensing minute ventilation to detect a patient's metabolic demand as an input for demand rate-variable cardiac pacers.

It is known that some patients suffering from cardiovascular illness cannot generate nerve signals to cause the cardiac muscle contractions which pump blood throughout their bodies. Artificial pacers have been developed to transmit signals to the patients' cardiac muscles and substitute for natural signals.

Changes in a patient's metabolic rate, caused for example by varying physical activity, create varying body demands for cardiovascular pumping. In response to the need for demand rate-variable pacers, different methods have been developed for sensing metabolic demands and adjusting the signal output of the pacer to the patient's heart. Variables which have been, or are being, studied as indicators of metabolic rate response in pacing include: venous oxygen saturation; venous Ph; stoke volume; right ventricular temperature; right ventricular pressure; QT interval; physical activity (i.e., gross body movement rates); and respiratory rate.

Of these variables, respiratory rate, and more specifically minute ventilation (defined as the product of the patient's respiration rate and the tidal volume of each breath, i.e. the volume of air breathed per minute), appears to be the most accurate measure of metabolic demand, since it is a parameter actually calculated by the patient's brain to set the heart pumping rate. A pacer having a sensing system designed to detect the patient's minute ventilation rate and to vary its own electrical pacing pulse rate in response thereto would desirably mimic the natural human body function.

One pacer apparatus for sensing ventilation rate disclosed in U.S. Pat. No. 4,567,892 involves the subcutaneous implantation of a pair of leads in the chest wall and measurement of changes in electrode impedance during respiration. Such sensing is effected by driving a pulsed current through a pair of leads and measuring with electrical circuitry the voltage drop of the current impulses to determine changes in electrical impedance. The drawback of the system disclosed in U.S. Pat. No. 4,567,892 is that an extra pair of leads must be implanted in the patient in addition to the normal pacing leads. Pacing leads may be installed transvenously into the patient's cardiovascular system, such as by inserting an atrial J-electrode in the patient's right atrium and it would also be desirable to implant ventilation sensors transvenously while implanting pacer leads.

It is an object of the present invention to sense the minute ventilation rate of a patient for use by a demand rate-variable pacer without installation of additional sensing leads.

It is another object of the invention to provide a minute ventilation sensing system and method for sensing minute ventilation which may be easily implanted by surgeons using known techniques.

If is a further object of the invention to create a minute ventilation sensing system and a method for sensing minute ventilation which may be implanted transvenously within the patient's cardiovascular system.

Lastly, it is an object of the invention to construct a minute ventilation sensing system and method for sensing minute ventilation which may be combined with known types of pacer leads, such as atrial J-electrodes, and may be implanted simultaneously with the other leads.

SUMMARY OF THE INVENTION

These objects have been attained by a minute ventilation sensing system constructed in accordance with the teachings of the present invention, which utilizes the method for sensing minute ventilation rate also taught by the present invention; the system and method provide for accurate sensing of the minute ventilation rate by detecting the frequency and amplitude of the patient's diaphragm motion. The sensor lead means and transducer means of the present invention can be transvenously implanted by surgeons in the cardiovascular system, using known implantation techniques or by any other desired implantation techniques that allow coupling of the sensor to any part of the body that moves in response to diaphragm motion during respiration.

The present invention features a sensing system for detecting the frequency and amplitude of motion of a patient's diaphragm comprising a transducer means for detecting movement, transvenously implantable in a patient's cardiovascular system; a lead means coupled to the transducer means, transvenously implantable in a patient's cardiovascular system; and a sensing instrument coupled to the lead means for correlating transducer movement with the frequency and amplitude of diaphragm motion.

The present invention also features a sensing system for detecting the frequency and amplitude of motion of a patient's diaphragm comprising a transducer means for detecting movement, transvenously implantable in a patient's cardiovascular system, having strain gauge means having variable elongation in response to movement; a lead means transvenously implantable in a patient's cardiovascular system, at least a portion of the lead means being implantable in a flexed configuration having a bend therein and a pair of opposing leg portions projecting from the bend and forming a gap therebetween, with the strain gauge being coupled to the lead means in the flexed portion thereof so that diaphragm motion causes arcuate rotation of the leg portions and varies elongation of the strain gauge means; and a demand rate-variable pacer coupled to the lead means for correlating transducer movement with the frequency and amplitude of the diaphragm motion.

The present invention also includes a method for sensing the frequency and amplitude of motion of a patient's diaphragm comprising transvenously implanting in a patient's cardiovascular system a transducer means capable of measuring movement frequency and amplitude; detecting the frequency and amplitude of movement of the transducer means; and correlating transducer movement with the frequency and amplitude of the patient's diaphragm movement.

While the preferred embodiments of the present invention provide for a sensing system having lead means and transducer means that are transvenously implantable in a patient's cardiovascular system as part of a pacer electrode, such as an atrial J-electrode, it should be understood that the sensing system lead means and transducer means of the present invention need not be implanted transvenously and need not be constructed as part of a pacer electrode.

DETAILED DESCRIPTION OF INVENTION

Figure 1:
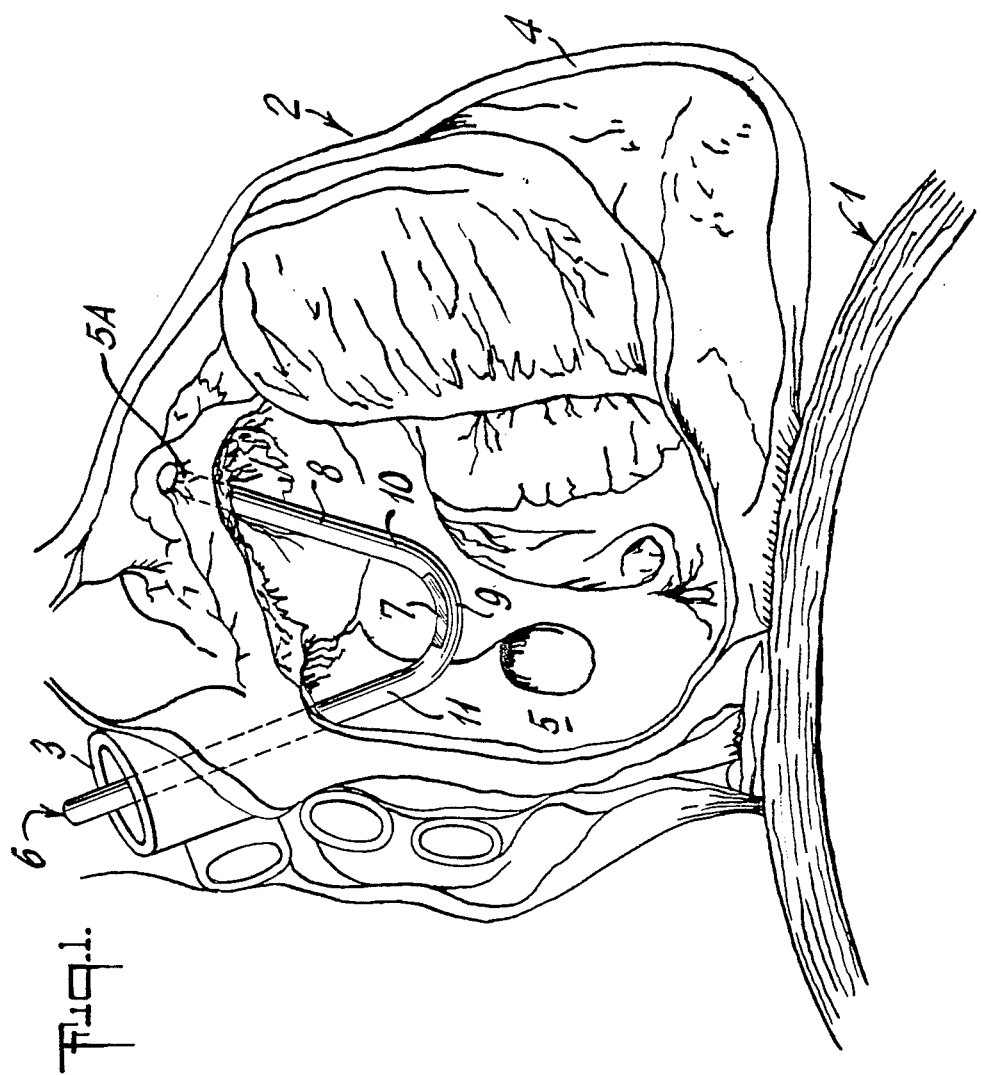
FIG. 1 is a schematic view of a cardium and diaphragm showing one embodiment of a minute ventilation sensing system lead means and transducer means constructed in accordance with the teachings of the present invention.

The present invention provides a sensing system for detecting the frequency and amplitude of motion of a patient's diaphragm, which comprises a transducer means for detecting movement, transvenously implantable in a patient's cardiovascular system; a lead means coupled to the transducer means, transvenously implantable in a patient's cardiovascular system; and a sensing instrument coupled to the lead means for correlating transducer movement with the frequency and amplitude of diaphragm motion.

The sensing system transducer means may comprise strain gauge means, which may be desirably embedded in the lead means, a piezoelectric crystal, or a pair of opposed capacitance plates having a gap between the plates that is variable in proportion to diaphragm motion.

The transducer means may also comprise a pulsed photoelectric signal generator and a photoelectric signal receiver for intercepting an electromagnetic signal transmitted by the generator, where the generator and receiver have a gap therebetween that is variable in proportion to diaphragm motion. The generator and the receiver may be semiconductor devices and at least one of the semiconductor devices may be a photodiode.

The lead means may be deformable in response to diaphragm motion. In some embodiments of the invention at least a portion of the lead means is implantable in a flexed configuration having a bend therein and a pair of opposing leg portions projecting from the bend and forming a gap therebetween, so that diaphragm motion causes arcuate rotation of the leg portions and varies the gap and the transducer means is in the flexed portion of the lead means.

The sensing instrument may be a demand rate-variable pacer and the transducer means and the lead means may be coupled to an atrial J-electrode.

In another embodiment of the invention, a sensing system is provided for detecting the frequency and amplitude of motion of a patient's diaphragm comprising a transducer means for detecting movement, transvenously implantable in a patients' cardiovascular system, having strain gauge means that varies elongation in response to movement; a lead means transvenously implantable in a patient's cardiovascular system, at least a portion of the lead means being implantable in a flexed configuration having a bend therein and a pair of opposing leg portions projecting from the bend and forming a gap therebetween, with the strain gauge being coupled to the lead means in the flexed portion thereof, so that diaphragm motion causes arcuate rotation of the leg portions and varies elongation of the strain gauge means; and a demand rate-variable pacer coupled to the lead means for correlating transducer movement with the frequency and amplitude of the diaphragm motion.

The present invention also provides a method for sensing the frequency and amplitude of motion of a patient's diaphragm which comprises transvenously implanting in a patient's cardiovascular system a transducer means capable of measuring movement frequency and amplitude; detecting the frequency and amplitude of movement of the transducer means; and correlating transducer movement with the frequency and amplitude of the patient's diaphragm movement. The transducer means may desirably be a strain gauge means.

In the method of the present invention, the implanting may be performed in a patient's cardiac chamber, cardiac atrium, pericardium, pericardial space, diaphragm or in one of a patient's hepatic veins.

In the method of the present invention, the detecting may comprise measuring a signal generated by the transducer in response to transducer movement and the signal measuring may include carrying the signal to the sensing instrument; the sensing instrument may be a demand rate-variable pacer.

The following examples are illustrative of the minute ventilation sensing system and method for sensing minute ventilation of the present invention, but they in no way are intended to restrict the scope of the claims hereto.

Figure 3:
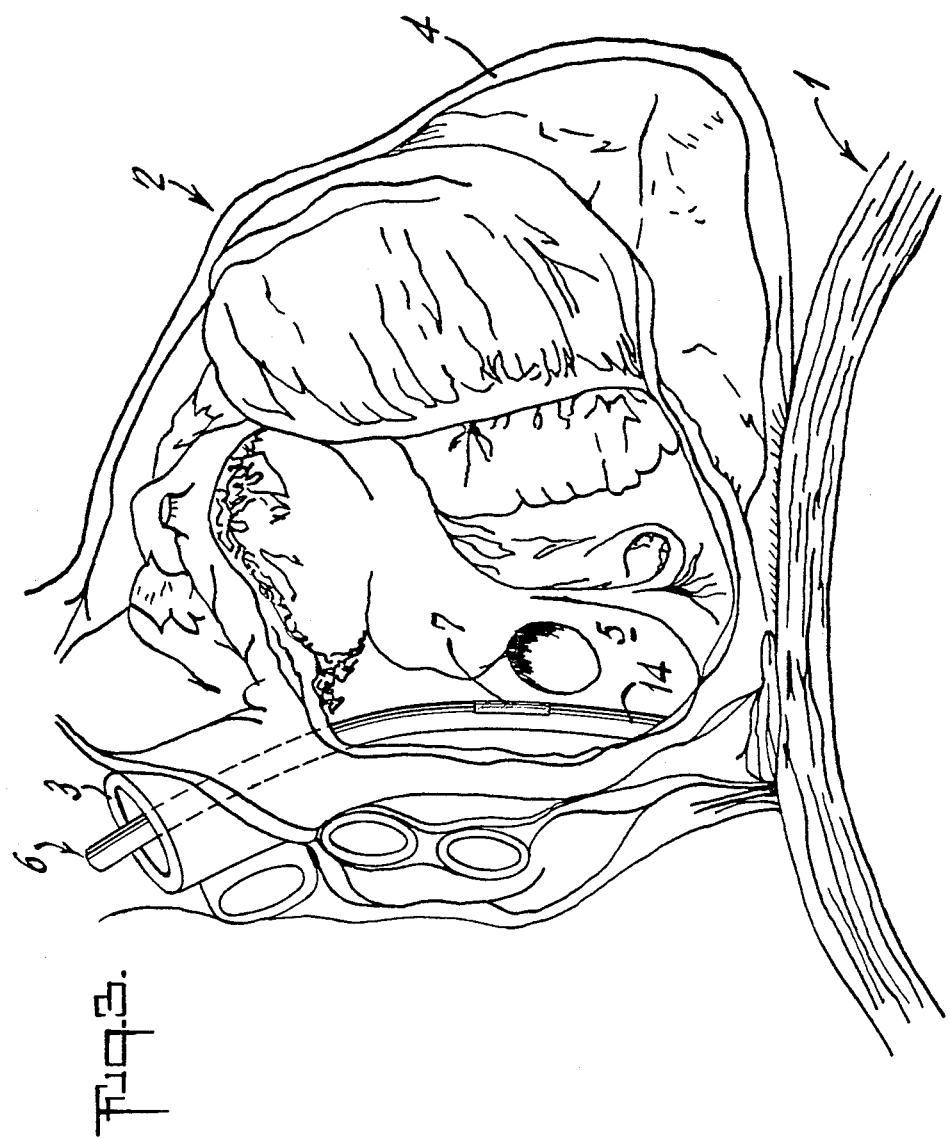
FIG. 3 is a schematic view similar to that shown in FIG. 1, showing another embodiment of a sensing system lead means and transducer means constructed in accordance with the teachings of the present invention.

Referring generally to FIGS. 1 and 3, there is shown schematically parts of the human body, including a diaphragm 1, a cardium or heart 2, a portion of the superior vena cava 3, the pericardium or heart covering 4 (also known as the pericardial sac 4), a cut-away view of the right atrium 5 and the right atrial appendage 5A. As is known, the diaphragm 1 is coupled to the pericardial sac 4 and diaphragm motion during respiration causes movement of the pericardial sac.

I have observed under fluoroscopy while implanting cardiac pacer systems that the pacer atrial lead moves along two axes; there is a lateral motion, i.e. from side to side which is caused primarily by cardiac activity and there is also vertical motion caused by diaphragm movement during respiration. As a surgeon skilled in the cardiac pacing apparatus implantation arts can appreciate, one of the steps in proper placement of an atrial J-electrode is to have the patient take a deep breath to assure that the atrial J-electrode does not descend further than the horizontal position during full inspiration. Vertical motion of the atrial J-electrode is caused by vertical pericardial displacement with the diaphragm.

Accordingly, as a teaching of the present invention, one implants a minute ventilation sensor of a sensing system comprising lead means coupled to a transducer that can sense vertical diaphragm motion by coupling the transducer to the diaphragm or any other body organ directly or indirectly coupled to the diaphragm, and coupling the lead means to a sensing instrument capable of correlating transducer movement to diaphragm movement. The sensing instrument need not be transvenously implantable.

It is a further teaching of the present invention that the minute ventilation sensor is transvenously implantable in a patient's cardiovascular system, such as in the hepatic veins, the subclavian vein, the internal jugular vein or any vascular structure coupled to the pericardial sac or the diaphragm. Transvenous implantation of the sensor lead means and transducer means in the right atrium is the preferred implantation technique, and avoids the need for thoracic surgery or additional pericutaneous implantation. However, any known or desired implantation technique may be utilized, including direct implantation into the pericardial sac or pericardial space by thoracic surgery or pericutaneous catherization and if desired, the sensor lead means and transducer means of the present invention may be implanted separately from the pacer leads.

Figure 2:
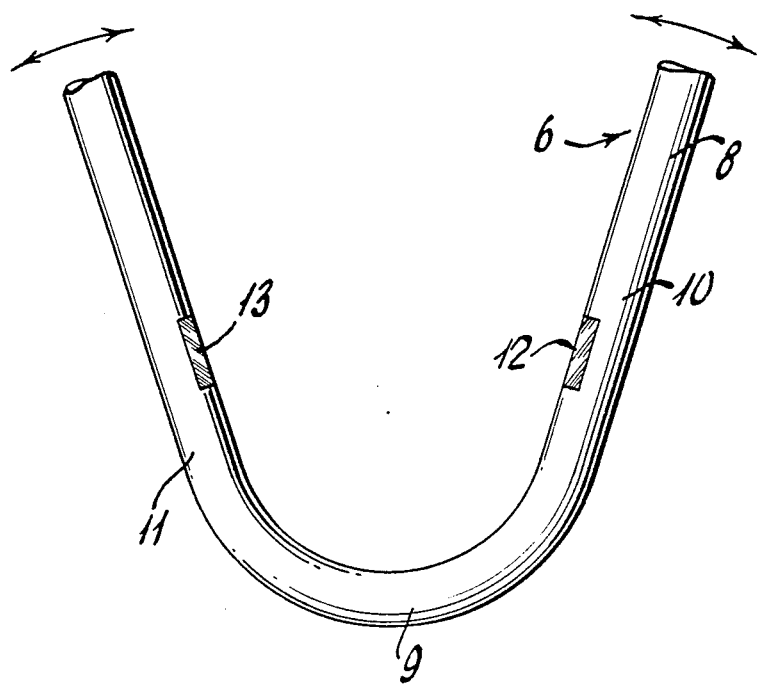
FIG. 2 is a schematic view of another embodiment of a minute ventilation sensing system lead means and transducer means constructed in accordance with the teachings of the present invention.

In a preferred embodiment of the invention, such as shown in FIGS. 1 and 2, the sensing system sensor 6 of the present invention includes transducer means 7 for detecting motion coupled to a lead means 8. The lead means is coupled to a sensing instrument 8A that correlates transducer 7 movement to diaphragm 1 movement. It is preferred that the lead means 8 perform as both a support structure for the transducer means and as a carrier of a signal generated by the transducer for transmission to the sensing instrument 8A. Preferably the lead means 8 is an atrial J-electrode, but any other type of transvenously implantable lead means can be utilized, so long as the lead is coupled to the transducer means and adapted for coupling to a sensing instrument of the sensing system, such as a demand rate-variable cardiac pacer, so that a signal generated by the transducer can be carried or transmitted to the sensing instrument.

The sensing instrument, as part of the sensing system correlates transducer means frequency and amplitude of movement signals to the patient's diaphragm movement.

In the preferred embodiment of FIG. 1, atrial J-electrode lead means 8 shown therein is implanted in the patient's right atrium 5, anchored to the superior vena cava 3 and the right atrial appendage 5A by known techniques; a portion of the lead means is implanted in a flexed configuration, having a bend 9 therein and a pair of opposing leg portions 10 and 11 which project from the bend and form a gap therebetween. Motion of the diaphragm 1, measured at a frequency and amplitude, causes vertical movement of the pericardial sac 4 and in turn causes arcuate rotation of the leg portions 10 and 11, so that the gap between the leg portions 10 and 11 opens and closes in response to the diaphragm movement.

The transducer means 7 is preferably a strain gauge of known construction that varies electrical resistance in response to deformation thereof. The strain gauge transducer 7 is preferably embedded in the lead means 8 along with wires (not shown) that are the carrier of the strain gauge output signal to the sensing instrument of the system. As shown in FIG. 1, if the strain gauge transducer 7 is affixed in the bend 9 of the lead, it will lengthen and shorten in response to arcuate movement of the opposing leg portions 10 and 11 and a change in the resistivity of the strain gauge will change output voltage from the strain gauge. By monitoring the strain gauge 7 output voltage amplitude signal with the sensing instrument 8A, the amplitude will be proportional to strain gauge deformation, which is in turn proportional to vertical movement of the pericardial sac 4 and the diaphragm 1. Periodic movement of the diaphragm during respiration will appear as a proportional periodic change in strain gauge 7 output voltage. The sensing instrument 8A can then correlate the amplitude and frequency of strain gauge 7 output voltage with the amplitude and frequency of the patient's diaphragm motion.

It is contemplated that other forms of transducer means 7 may be utilized in an atrial J-electrode lead means 8 shown in FIG. 1, or any other form of lead means. Other suitable transducer means include piezoelectric crystals or even a pair of opposed transducer means 12 and 13 as shown in FIG. 2. Examples of such opposed transducer means can include a pair of capacitance plates having a gap between the plates that varies in proportion to diaphragm motion or a pulsed photoelectric signal generator and photoelectric signal receiver adapted for sensing an optical signal transmitted by the generator. As one skilled in the art can appreciate, if the opposed transducers 12 and 13 are capacitance plates, and a current is passed between the plates, a variation in the gap between the plates will change the output voltage between the plates.

Similarly, if the opposed transducers 12 and 13 are a paired photoelectric signal generator and receiver (such as photodiodes or other types of semiconductor devices), if a pulsed light or other electromagnetic signal is passed between the generator and receiver, varying the gap between the paired transducers 12 and 13 will change the actual time necessary for the receiver to sense the generator signal and the sensing instrument 8A can correlate the time changes caused by transducer movement with diaphragm movement. The present invention includes any kind of transducer means that can detect motion and that is transvenously implantable into a patient's body.

FIG. 3 shows another embodiment of lead means 6 that can be passed transvenously, for example through subclavian vein, and which is anchored for example within the right atrium 5, by known techniques. As shown in FIG. 3, vertical motion of the diaphragm, coupled to the pericardial sac causes vertical motion within the atrium and in turn causes elongation and contraction deformation movement of lead 14 that is sensed by transducer 7. Any of the above-described transducers that can sense elongation and contraction movement of lead 14 can be used in this embodiment.

EXAMPLE

A minute ventilation sensing system lead means and transducer means, such as shown in FIG. 1, were transvenously implanted in a dog by entering the dog's internal jugular vein and routing the sensor, coupled to an atrial J-electrode, through the superior vena cava and positioning it in the right atrial appendage. The transducer means was a strain gauge block constructed of a carbonized rubber material sold under the trademark FLEXIGAUGE, manufactured in Glasgow, Scotland, that was tied to the atrial J-electrode. The lead means in this example were wires embedded into each end of the rubber strain gauge and tied to the exterior of the atrial J-electrode.

Upon implantation into the dog, the minute ventilation sensor lead means was coupled to a system sensing instrument, which was a strip recorder displaying time on the ordinate and voltage on the abcissa. Both AC and DC voltage readings showed periodic repetitions in amplitude which were correlated to the frequency and amplitude of the dog's respiration.

What is claimed is:

1. A sensing system for detecting the frequency and amplitude of motion of a patient's diaphragm comprising:

a transducer means for detecting vertical movements of the patient's pericardial sac, transvenously implantable in a patient's cardiovascular system;

a lead means coupled to the transducer means, transvenously implantable in a patient's cardiovascular system, and a sensing instrument means for correlating transducer movement detection with the frequency and amplitude of diaphragm motion coupled to the lead means and the transducer means.

2. The sensing system of claim 1, wherein the transducer means is a strain gauge means.

3. The sensing system of claim 2, wherein the strain gauge means is embedded in the lead means.

4. The sensing system of claim 1, wherein the transducer means is a piezoelectric crystal.

5. The sensing system of claim 1, wherein the lead means is deformable in response to pericardial sac motion, the transducer means is a pair of capacitance plates mounted on the lead means with a gap between the plates that is variable in proportion to lead means deformation.

6. The sensing system of claim 1, wherein the lead means is deformable in response to pericardial sac motion, the transducer means is a pulsed photoelectric signal receiver for intercepting a signal transmitted by the generator, and the generator and receiver are mounted on the lead means with a gap therebetween that is variable in proportion to lead means deformation.

7. The sensing system of claim 6, wherein the generator and the receiver are semiconductor devices.

8. The sensing system of claim 7, wherein at least one of the semiconductor devices is a photodiode.

9. The sensing system of claim 1, wherein the lead means is deformable in response to diaphragm motion.

10. The sensing system of claim 1, wherein:

at least a portion of the lead means is implantable in a flexed configuration having a bend therein and a pair of opposing leg portions projecting from the bend and forming a gap, therebetween, so that diaphragm motion causes lead deformation by causing arcuate rotation of the leg portions and varies the gap; and the transducer means is in the flexed portion of the lead means and detects lead deformation.

11. The sensing system of claim 1, wherein the sensing instrument means is a demand rate-variable pacer.

12. The sensing system of claim 1, wherein the lead means includes an atrial J-electrode.

13. A sensing system for detecting the frequency and amplitude of motion of a patient's diaphragm comprising:

a strain gauge means for detecting vertical movements of the patient's pericardial sac, transvenously implantable in a patients' cardiovascular system, having variable elongation in response to movement;

a lead means transvenously implantable in a patient's cardiovascular system, at least a portion of the lead means being implantable in a flexed configuration having a bend therein and a pair of opposing leg portions projecting from the bend and forming a gap therebetween, with the strain gauge being coupled to the lead means in the flexed portion thereof so that vertical movements of the pericardial sac cause arcuate rotation of the leg portions and varies elongation of the strain gauge means; and a demand rate-variable pacer coupled to the lead means and the strain gauge means for correlating strain gauge elongation with the frequency and amplitude of the diaphragm motion.

14. The sensing of system of claim 13, wherein the lead means includes an atrial J-electrode.

15. A method for sensing the frequency and amplitude of motion of a patient's diaphragm comprising:

transvenously implanting in a patient's cardiovascular system a transducer means capable of measuring frequency and amplitude of vertical movements of the patient's pericardial sac;

detecting the frequency and amplitude of movement measurements of the transducer means; and correlating transducer movement measurements with the frequency and amplitude of the patient's diaphragm movement.

16. The method of claim 15, wherein the transducer means is a strain gauge means.

17. The method of claim 15, wherein the implanting is performed in a patient's cardiac chamber.

18. The method of claim 15, wherein the implanting is performed in a patient's cardiac atrium.

19. The method of claim 15, wherein the implanting is performed in a patient's hepatic vein.

20. The method of claim 15, wherein the detecting comprises measuring a signal generated by the transducer in response to transducer movement.

21. The method of claim 20, wherein the signal measuring includes carrying the signal to a sensing instrument.

22. The method of claim 21, wherein the sensing instrument is a demand rate-variable pacer.

* * * * *